United States Patent
Kyani et al.

(10) Patent No.: US 12,109,420 B2
(45) Date of Patent: Oct. 8, 2024

(54) SYSTEMS AND METHODS FOR OPTIMIZED WAVEFORM GENERATION

(71) Applicant: Advanced Neuromodulation Systems, Inc., Plano, TX (US)

(72) Inventors: Anahita Kyani, Plano, TX (US); Jagatkumar Shah, Lake in the Hills, IL (US); Douglas Lautner, Frisco, TX (US); Ali Taheri, Sylmar, CA (US); Simeng Zhang, Frisco, TX (US); Yagna Pathak, Skokie, IL (US); Erika Ross, Dallas, TX (US); Hyun-Joo Park, Frisco, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 122 days.

(21) Appl. No.: 17/091,469

(22) Filed: Nov. 6, 2020

(65) Prior Publication Data

US 2022/0143410 A1    May 12, 2022

(51) Int. Cl.
*A61N 1/00* (2006.01)
*A61B 5/0215* (2006.01)
*A61N 1/365* (2006.01)

(52) U.S. Cl.
CPC ........ *A61N 1/36564* (2013.01); *A61B 5/0215* (2013.01)

(58) Field of Classification Search
None
See application file for complete search history.

(56) References Cited

U.S. PATENT DOCUMENTS

| | | | |
|---|---|---|---|
| 5,370,672 A | 12/1994 | Fowler et al. | |
| 5,938,690 A | 8/1999 | Law et al. | |
| 8,694,115 B2* | 4/2014 | Goetz | A61N 1/37247 607/2 |
| 8,918,177 B2* | 12/2014 | Gauthier | A61N 1/37247 607/46 |
| 2004/0199215 A1 | 10/2004 | Lee et al. | |
| 2004/0199216 A1 | 10/2004 | Lee et al. | |
| 2004/0199217 A1 | 10/2004 | Lee et al. | |
| 2004/0199218 A1 | 10/2004 | Lee et al. | |
| 2004/0215286 A1 | 10/2004 | Stypulkowski | |

(Continued)

*Primary Examiner* — John R Downey
*Assistant Examiner* — Anant A Gupta
(74) *Attorney, Agent, or Firm* — Armstrong Teasdale LLP

(57) ABSTRACT

Provided herein is a computing system for optimizing a waveform, in communication with an implantable pulse generator, and including a computing device including a memory device and a processor communicatively coupled to the memory device. The processor is configured to: retrieve historical waveform data associated with a plurality of waveforms used in therapeutic sessions for a plurality of patients, the historical waveform data including a plurality of waveform parameters; analyzing the historical waveform data to determine preferred waveform parameters; determining that a patient is starting a new therapeutic session using the patient therapeutic device; displaying each of the preferred waveform parameters; prompting the user to accept or modify the displayed waveform parameters; optimizing the waveform parameters for the therapeutic session; and transmitting the optimized waveform parameters to the patient therapeutic device to start the therapeutic session.

18 Claims, 6 Drawing Sheets

(56) References Cited

U.S. PATENT DOCUMENTS

| | | | |
|---|---|---|---|
| 2012/0179071 A1* | 7/2012 | Skelton | G16Z 99/00 600/595 |
| 2013/0023950 A1* | 1/2013 | Gauthier | A61N 1/37247 607/46 |
| 2014/0277282 A1* | 9/2014 | Jaax | A61N 1/36139 607/59 |
| 2017/0224990 A1* | 8/2017 | Goldwasser | A61N 1/0476 |
| 2019/0262610 A1 | 8/2019 | Kent et al. | |

* cited by examiner

SYSTEMS AND METHODS FOR OPTIMIZED WAVEFORM GENERATION

A. FIELD OF THE DISCLOSURE

The present disclosure relates generally to neuromodulation systems, and more particularly to optimizing the generation of neuromodulation waveforms.

B. BACKGROUND ART

Neurostimulation is an established neuromodulation therapy for the treatment of chronic pain and movement disorders. For example, neurostimulation has been shown to improve cardinal motor symptoms of Parkinson's Disease (PD), such as bradykinesia, rigidity, and tremors in addition to relieving symptoms of failed back surgery syndrome (FBSS) and complex regional pain syndrome (CRPS). A subset of neurostimulation types include deep brain stimulation (DBS), spinal cord stimulation (SCS), and Dorsal Root Ganglion (DRG) stimulation.

Recently, novel waveform therapy for neuromodulation has become a topic of interest, and there is a desire to create sophisticated waveforms. However, at least some known systems are only capable of producing a default waveform that cannot be modified by patients. Patients may require waveforms other than the default waveform to fit their therapeutic needs. For known systems, the patients' having to visit a clinician each time the waveform requires modification is time intensive, and may therefore dissuade the patient from using neuromodulation. Further, the waveforms are largely modified by trial-and-error, where one parameter of the waveform is changed while the other parameters are unchanged, such that the clinician has to try a large number of waveform parameter combinations before the optimal waveform is chosen. Thus, within these constraints of at least some known systems, it may be difficult and time-intensive for patients to receive neuromodulation therapy Accordingly, it would be desirable to provide a system that facilitates optimizing waveforms for neuromodulation and provides a user interface for patients to modify the waveforms themselves.

BRIEF SUMMARY OF THE DISCLOSURE

In one embodiment, the present disclosure is directed to a computing system for optimizing a waveform in communication with an implantable pulse generator. The computing system includes a computing device including a memory device and a processor communicatively coupled to the memory device. The processor is configured to: retrieve, from the memory device, historical waveform data associated with a plurality of waveforms used in therapeutic sessions for a plurality of patients, the historical waveform data including a plurality of waveform parameters; analyze the historical waveform data to determine preferred waveform parameters; determine that a patient is starting a new therapeutic session using the patient therapeutic device; display, on the user interface, each of the preferred waveform parameters; prompt the user to accept or modify the displayed waveform parameters; optimize, based upon the user input, the waveform parameters for the therapeutic session; and transmit the optimized waveform parameters to the patient therapeutic device to start the therapeutic session.

In another embodiment, the present disclosure is directed to a method for optimizing a waveform implemented by a computing system in communication with an implantable pulse generator. The computing system includes a processor in communication with a memory device. The method includes: retrieving, from the memory device, historical waveform data associated with a plurality of waveforms used in therapeutic sessions for a plurality of patients, the historical waveform data including a plurality of waveform parameters; analyzing the historical waveform data to determine preferred waveform parameters; determining that a patient is starting a new therapeutic session using the patient therapeutic device; displaying, on the user interface, each of the preferred waveform parameters; prompting the user to accept or modify the displayed waveform parameters; optimizing, based upon the user input, the waveform parameters for the therapeutic session; and transmitting the optimized waveform parameters to the patient therapeutic device to start the therapeutic session.

In another embodiment, the present disclosure is directed to non-transitory computer-readable media having computer-executable instructions thereon. When executed by a processor of a computing device communicatively coupled to a memory device, the computer-executable instructions cause the processor of the computing device to: retrieve, from the memory device, historical waveform data associated with a plurality of waveforms used in therapeutic sessions for a plurality of patients, the historical waveform data including a plurality of waveform parameters; analyze the historical waveform data to determine preferred waveform parameters; determine that a patient is starting a new therapeutic session using the patient therapeutic device; display, on the user interface, each of the preferred waveform parameters; prompt the user to accept or modify the displayed waveform parameters; optimize, based upon the user input, the waveform parameters for the therapeutic session; and transmit the optimized waveform parameters to the patient therapeutic device to start the therapeutic session.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

Figure 1:
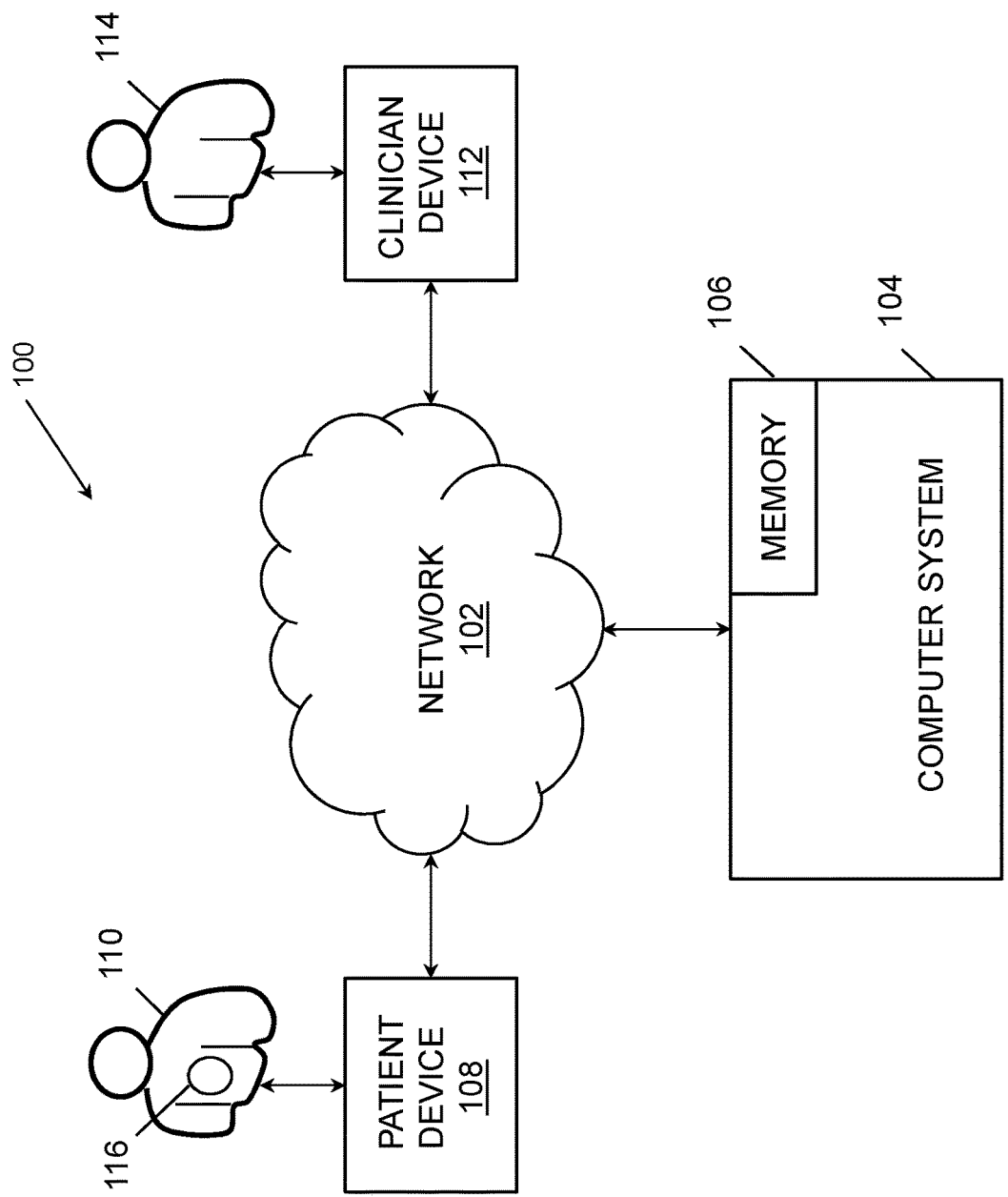
FIG. 1 is a diagram of one embodiment of a system for neuromodulation therapy.

Systems and methods are disclosed for optimizing the generation of waveforms for an implantable medical device (e.g., an implantable pulse generator) of a neuromodulation system.

Neurostimulation systems, which include neuromodulation systems, include devices that generate electrical pulses and deliver the pulses to nervous tissue of a patient to treat a variety of disorders. One category of neurostimulation systems is deep brain stimulation (DBS). In DBS, pulses of electrical current are delivered to target regions of a subject's brain, for example, for the treatment of movement and effective disorders such as PD and essential tremor. Another category of neurostimulation systems is spinal cord stimulation (SCS) for the treatment of chronic pain and similar disorders.

A waveform optimization system includes a computer system, a network, a clinician device, and a patient device communicatively coupled to the implantable medical device. The network includes a plurality of historical waveform data relating to waveforms and the corresponding parameters of the waveforms used in past neuromodulation therapy sessions. The computer system is configured to analyze the historical waveform data to determine preferred waveform parameters. Further, the computer system is configured to display the preferred waveform parameters to a programming device associated with the implantable medical device (e.g., a patient device of a patient, a clinician device of a clinician, or any other suitable device) and allow the patient and/or clinician to modify the preferred waveform parameters. The computer system is configured to optimize the waveform parameters based upon the modifications from the patient and/or clinician and transmit the optimized waveform parameters to the programming device. The programming device is communicatively coupled to the implantable medical device, and the programming device transmits the optimized waveform parameters to the implantable medical device to begin a neuromodulation therapy session.

As compared to at least some known systems, the systems and methods described herein enable optimization of waveform parameters, the parameters including a shape of the waveform, for an implantable pulse generator used in neuromodulation therapy. This enables quick and efficient generation of waveform parameters optimized to patients, which is not available in known systems.

More specifically, the embodiments described herein use historical waveform data to determine preferred waveform parameters of patients in past neuromodulation therapy sessions. The preferred waveform parameters are displayed to the patient and/or the clinician, and the patient and/or clinician provides input (e.g., modifications) regarding the preferred waveform parameters. Optimized waveforms are generated based upon the preferred waveform parameters and the patient and/or clinician input, such that the patient is able to quickly begin the part of neuromodulation therapy session where the waveforms are delivered, and the waveforms are optimized to the needs of the patient. At least some known systems do not provide such quick optimization.

Multiple types of waveforms can be used in neuromodulation therapies, and the types of waveforms are usually chosen based upon patient preference and the progress of the patient using the neuromodulation therapy. For example, tonic (i.e., continuous pulses) waveforms and burst (i.e., packets of high-frequency pulses) waveforms may be used. The parameters of tonic waveforms include frequency, pulse-width, and amplitude. The parameters of burst waveforms include number of pulses, intra-burst frequency, inter-burst frequency, pulse-width, and amplitude.

In at least some known systems, patients are required to visit clinicians to determine the best waveform parameters for the neuromodulation therapy of the patients. The clinicians typically determine the best waveform parameters through a "guess-and-check" approach. That is, if the waveform has three parameters (e.g., amplitude, frequency, and pulse-width), the clinician must optimize each of the parameters in relation to the other two parameters. For example, if the system has ten amplitude levels, three frequency levels, and four pulse-width levels, the clinician would have to evaluate 120 waveform parameter combinations with the patient to determine the best waveform for the patient. Waveforms with more than three parameters might require even more repetitions of trial and error for the clinician.

The embodiments described herein allow the patient and clinician to efficiently and rationally optimize the waveform parameters before the patient starts neuromodulation therapy such that a minimal amount of modification is needed for the patient to get the best results from the neuromodulation therapy.

Referring now to the drawings, and in particular to FIG. 1, a system is indicated generally at 100. One or more embodiments of a neuromodulation therapy session may be implemented in system 100, as described herein. In general, "neuromodulation therapy" may involve any neurostimulation or neuromodulation therapy type (e.g., DBS, SCS, etc.) provided through an implantable medical device of a patient with a clinician, a medical professional, or a healthcare provider managing the therapy.

System 100 includes a network 102 that is communicatively coupled to a computer system 104 (including at least a data storage-memory 106), a patient device 108 of a patient 110, and a clinician device 112 of a clinician 114. Computer system 104 may further include conventional interface components, such as the components shown in FIG. 6, among other components. In the illustrated embodiment, network 102 is communicatively coupled to one patient device 108 and one clinician device 112. However, in other embodiments, network 102 is communicatively coupled with a plurality of patient devices 108 of patients 110 and clinician devices 112 of clinician devices 114.

Network 102 may include any combination or sub-combination of a public packet-switched network infrastructure (e.g., the Internet or worldwide web, also sometimes referred to as the "cloud"), private packet-switched network infrastructures such as Intranets and enterprise networks, health service provider network infrastructures, and the like, any of which may span or involve a variety of access networks, backhaul and core networks in an end-to-end network architecture arrangement between one or more patients, e.g., patient(s) 110, one or more authorized clinicians, healthcare professionals, or agents thereof, e.g., generally clinician(s) 114, and the computer system 104.

Example patient(s) 110, each having a suitable implantable device 116, may be provided with a variety of corresponding external devices for controlling, programming, otherwise (re)configuring the functionality of respective implantable medical device(s) 116, as is known in the art. Such external devices associated with patient(s) 110 are referred to herein as patient devices 108, and may include a variety of user equipment (UE) devices. By way of example, patient devices 116 may include smartphones, tablets or phablets, laptops/desktops, handheld/palmtop computers, wearable devices such as smart glasses and smart watches, personal digital assistant (PDA) devices, smart digital assistant devices, etc. As such, patient devices 108 may include various types of communications circuitry or interfaces to effectuate wired or wireless communications, short-range and long-range radio frequency (RF) communications, magnetic field communications, Bluetooth communications, etc., using any combination of technologies, protocols, and the like, with external networked elements and/or respective implantable medical devices 116 corresponding to patient(s) 110.

Similarly, clinicians 114 may be provided with a variety of external devices for controlling, programming, otherwise (re)configuring or providing therapy operations with respect to one or more patients 110 mediated via respective implantable medical device(s) 116, in a local therapy session and/or remote therapy session, depending on implementation and use case scenarios. External devices associated with clinicians 114, referred to herein as clinician devices 112, may include a variety of UE devices, tethered or untethered, similar to patient devices 108. Clinician devices 112 may therefore also include smartphones, tablets or phablets, laptops/desktops, handheld/palmtop computers, wearable devices such as smart glasses and smart watches, personal digital assistant (PDA) devices, smart digital assistant devices, etc. Clinician devices 112 may also include various types of communications circuitry or interfaces to effectuate wired or wireless communications, short-range and long-range radio frequency (RF) communications, magnetic field communications, Bluetooth communications, etc., using any combination of technologies, protocols, and the like, with external networked elements and/or respective implantable medical devices 116 and/or patient devices 108 corresponding to patient(s) 110.

In the embodiments described herein, implantable medical device 116 may be any suitable medical device. For example, implantable medical device may be a neurostimulation device (e.g., a neuromodulation device) that generates electrical pulses and delivers the pulses to nervous tissue of a patient to treat a variety of disorders, as described further with respect to FIG. 2.

Although implantable medical device 116 is described in the context of a neurostimulation device herein, those of skill in the art will appreciate that implantable medical device 116 may be any type of implantable medical device.

In the embodiments described herein, computer system 104, patient devices 108, and clinician devices 112 transmit and receive data from network 102, which may act as a repository. Accordingly, computer system 104, patient devices 108, and clinician devices 112 are communicatively coupled to one another through network 102.

In the exemplary embodiment, patient devices 108 and/or clinician devices 112 transmit historical waveform data including historical waveform parameters (e.g., amplitude, frequency, pulse-width, intra-burst frequency, inter-burst frequency, number of pulses, etc.) associated with past neuromodulation therapy sessions of patients 110 to network 102 for storage. Computer system 104 retrieves the historical waveform data and analyzes the historical waveform data to determine preferred waveform parameters of patients 110, as described herein. Computer system 104 transmits the preferred waveform parameters to patient device 108 through network 102 to be displayed to patient 110 (e.g., through a user interface). Patient 110 accepts and/or modifies the waveform parameters, and computer system 104 optimizes the waveform parameters based upon patient 110 input. Once the waveform parameters are sufficiently optimized by computer system 104 and accepted by patient 110, computer system 104 transmits the optimized waveform parameters to patient device 108 such that patient device 108 may control and/or configure implantable medical device 116 according to the optimized waveform parameters. For ease and clarity of describing the systems and methods of the disclosure, it is disclosed herein that the patient 110 accepts and/or modifies the waveform parameters from the computer system through the patient device 108. However, it should be understood from the disclosure provided herein that the patient 110, the clinician 112, or any other suitable user can accept and/or modify the waveform parameters for the implantable medical device 116 through any suitable programmable device, such as, for example, the patient device 108, the clinician device 112, or any other user device.

Accordingly, system 100 provides a system for optimizing waveform parameters for patients (e.g., patients 110) using neuromodulation therapy. Due to computer system 104 having access to a large number of historical waveform data records through network 102, computer system 104 is configured to efficiently and logically optimize waveform parameters for patients 110 starting new neuromodulation therapy sessions. Further, computer system 104 receives patient input regarding the waveform parameters and optimizes the waveform parameters based upon the patient input such that the neuromodulation therapy is dynamic and interactive.

Figure 2:
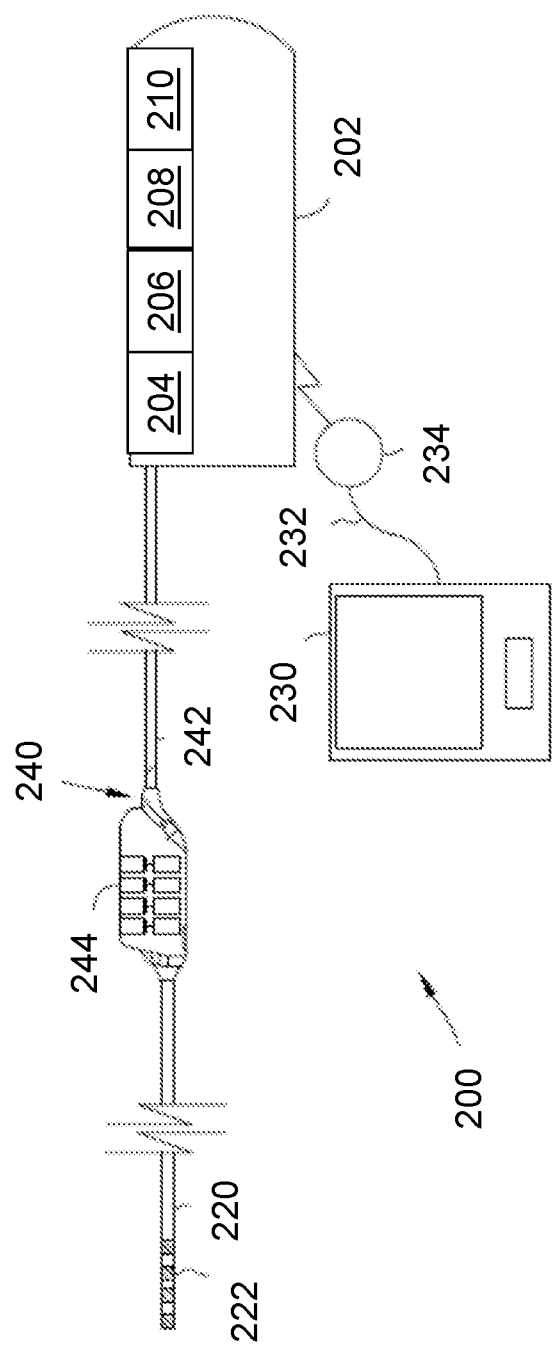
FIG. 2 is a schematic view of one embodiment of an implantable medical device system that may be used in the system shown in FIG. 1.

FIG. 2 illustrates an example stimulation system 200 that may be used in system 100, shown in FIG. 1. Specifically, stimulation system 200 may relate to patient device 108 and/or implantable medical device 116, as shown in FIG. 1, of system 100.

Stimulation system 200 generates electrical pulses for application to tissue of a patient (e.g., patient 110, shown in FIG. 1), or subject, according to one embodiment. System 200 includes an implantable pulse generator (IPG) 202 that is adapted to generate electrical pulses for application to tissue of a patient. Alternatively, system 200 may include an external pulse generator (EPG) positioned outside the patient's body. IPG 202 typically includes a metallic housing (or can) that encloses a controller 204, pulse generating circuitry 206, a battery 208, far-field and/or near field communication circuitry 210, and other appropriate circuitry and components of the device. Controller 204 typically includes a microcontroller or other suitable processor for controlling the various other components of the device. Software code is typically stored in memory of IPG 202 for execution by the microcontroller or processor to control the various components of the device.

IPG 202 may comprise one or more attached extension components 240 or be connected to one or more separate extension components 240. Alternatively, one or more stimulation leads 220 may be connected directly to IPG 202. Within IPG 202, electrical pulses are generated by pulse generating circuitry 206 and are provided to switching circuitry. The switching circuit connects to output wires, traces, lines, or the like (not shown) which are, in turn, electrically coupled to internal conductive wires (not shown) of a lead body 242 of extension component 240. The conductive wires, in turn, are electrically coupled to electrical connectors (e.g., "Bal-Seal" connectors) within connector portion 244 of extension component 240. The terminals of one or more stimulation leads 220 are inserted within connector portion 244 for electrical connection with respective connectors. Thereby, the pulses originating from IPG 202 and conducted through the conductors of lead body 242 are provided to stimulation lead 220. The pulses are then conducted through the conductors of lead 220 and applied to tissue of a patient via electrodes 222. Any suitable known or later developed design may be employed for connector portion 244.

For implementation of the components within IPG 202, a processor and associated charge control circuitry for an implantable pulse generator is described in U.S. Pat. No.

7,571,007, entitled "SYSTEMS AND METHODS FOR USE IN PULSE GENERATION," which is incorporated herein by reference. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

An example and discussion of "constant current" pulse generating circuitry is provided in U.S. Patent Publication No. 2006/0170486 entitled "PULSE GENERATOR HAVING AN EFFICIENT FRACTIONAL VOLTAGE CONVERTER AND METHOD OF USE," which is incorporated herein by reference. One or multiple sets of such circuitry may be provided within IPG 202. Different pulses on different electrodes may be generated using a single set of pulse generating circuitry using consecutively generated pulses according to a "multi-stimset program" as is known in the art. Alternatively, multiple sets of such circuitry may be employed to provide pulse patterns that include simultaneously generated and delivered stimulation pulses through various electrodes of one or more stimulation leads as is also known in the art. Various sets of parameters may define the pulse characteristics and pulse timing for the pulses applied to various electrodes as is known in the art. Although constant current pulse generating circuitry is contemplated for some embodiments, any other suitable type of pulse generating circuitry may be employed such as constant voltage pulse generating circuitry.

Stimulation lead(s) 220 may include a lead body of insulative material about a plurality of conductors within the material that extend from a proximal end of lead 220 to its distal end. The conductors electrically couple a plurality of electrodes 222 to a plurality of terminals (not shown) of lead 220. The terminals are adapted to receive electrical pulses and the electrodes 222 are adapted to apply stimulation pulses to tissue of the patient. Also, sensing of physiological signals may occur through electrodes 222, the conductors, and the terminals. Additionally or alternatively, various sensors (not shown) may be located near the distal end of stimulation lead 220 and electrically coupled to terminals through conductors within the lead body 242. Stimulation lead 220 may include any suitable number and type of electrodes 222, terminals, and internal conductors.

Controller device 230, which may relate to patient device 108, may be implemented to recharge battery 208 of IPG 202 (although a separate recharging device could alternatively be employed). A "wand" 232 may be electrically connected to controller device through suitable electrical connectors (not shown). The electrical connectors are electrically connected to coil 234 (the "primary" coil) at the distal end of wand 232 through respective wires (not shown). Typically, coil 234 is connected to the wires through capacitors (not shown). Also, in some embodiments, wand 232 may comprise one or more temperature sensors for use during charging operations.

The patient then places the primary coil 234 against the patient's body immediately above the secondary coil (not shown), i.e., the coil of the implantable medical device. Preferably, the primary coil 234 and the secondary coil are aligned in a coaxial manner by the patient for efficiency of the coupling between the primary and secondary coils. Controller device 230 generates an AC-signal to drive current through coil 234 of wand 232. Assuming that primary coil 234 and secondary coil are suitably positioned relative to each other, the secondary coil is disposed within the magnetic field generated by the current driven through primary coil 234. Current is then induced by a magnetic field in the secondary coil. The current induced in the coil of the implantable pulse generator is rectified and regulated to recharge the battery of IPG 202. The charging circuitry may also communicate status messages to controller device 230 during charging operations using pulse-loading or any other suitable technique. For example, controller device 230 may communicate the coupling status, charging status, charge completion status, etc.

External controller device 230 is also a device that permits the operations of IPG 202 to be controlled by a user after IPG 202 is implanted within a patient, although in alternative embodiments separate devices are employed for charging and programming. Also, multiple controller devices may be provided for different types of users (e.g., the patient or a clinician). Controller device 230 can be implemented by utilizing a suitable handheld processor-based system that possesses wireless communication capabilities. Software is typically stored in memory of controller device 230 to control the various operations of controller device 230. Also, the wireless communication functionality of controller device 230 can be integrated within the handheld device package or provided as a separate attachable device. The interface functionality of controller device 230 is implemented using suitable software code for interacting with the user and using the wireless communication capabilities to conduct communications with IPG 202.

Controller device 230 preferably provides one or more user interfaces to allow the user to operate IPG 202 according to one or more stimulation programs to treat the patient's disorder(s). Each stimulation program may include one or more sets of waveform parameters including pulse amplitude, pulse width, pulse frequency or inter-pulse period, pulse repetition parameter (e.g., number of times for a given pulse to be repeated for respective stimset during execution of program), etc. In the methods and systems described herein, waveform parameters may include, for example, a number of pulses in a burst (e.g., 3, 4, or 5 pulses per burst), an intra-burst frequency (e.g., 500 Hz), an inter-burst frequency (e.g., 40 Hz), and a delay between the pulses in a burst (e.g., less than 1 millisecond (ms)). In the exemplary embodiment, the waveform parameters are optimized by computer system 104, shown in FIG. 1.

IPG 202 modifies its internal parameters in response to the control signals from controller device 230 to vary the stimulation characteristics of stimulation pulses transmitted through stimulation lead 220 to the tissue of the patient. Neurostimulation systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are incorporated herein by reference. Example commercially available neurostimulation systems include the EON MINI™ pulse generator and RAPID PROGRAMMER™ device from Abbott Laboratories.

For example, waveforms generated using the systems and methods described herein may approximate sine waves, triangle waves, noise spectrums, etc. The embodiments described herein may be implemented within both SCS and DBS stimulation systems.

Figure 3:
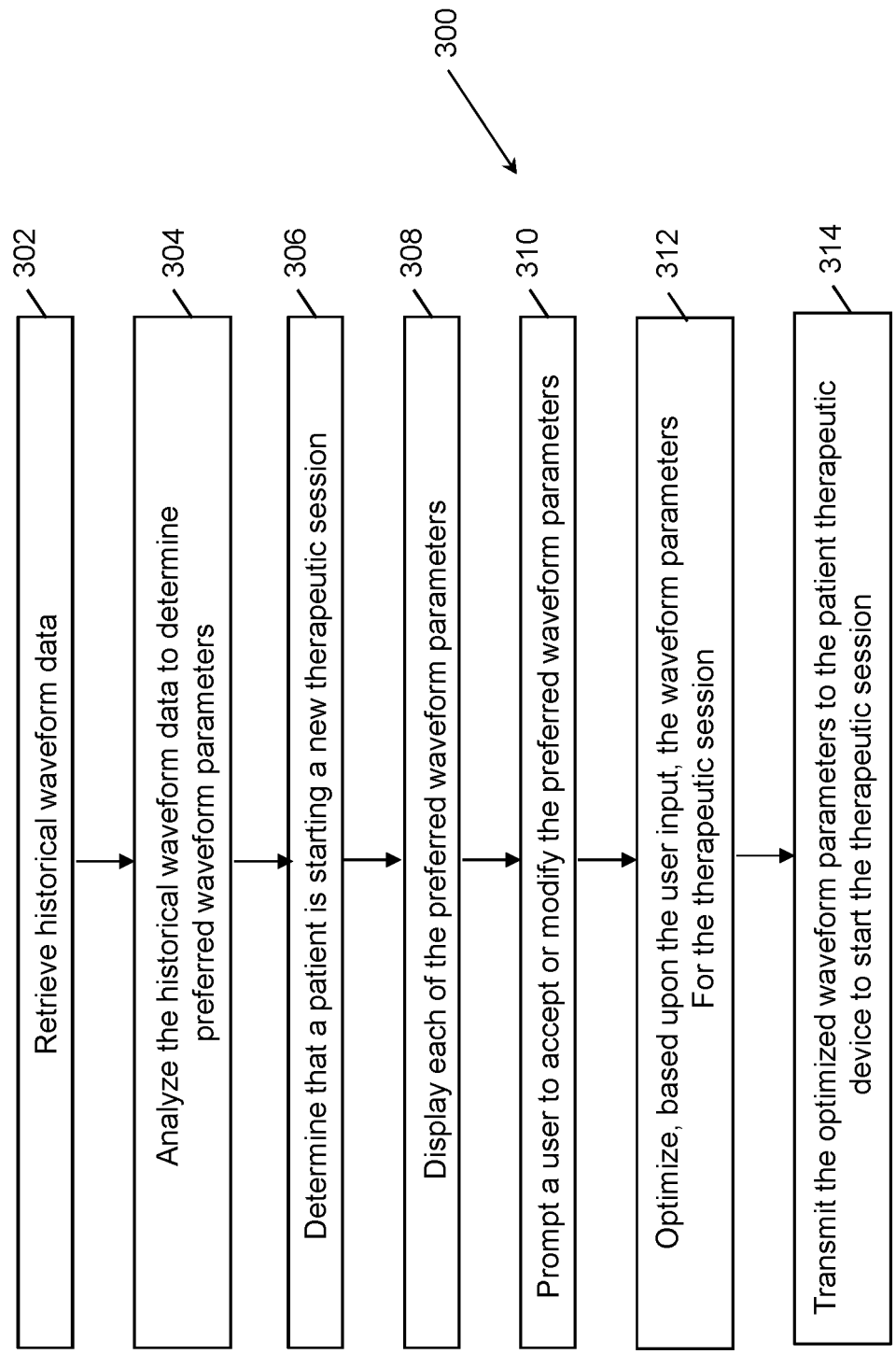
FIG. 3 is a flow diagram of one embodiment of optimizing a waveform for an implantable medical device.

FIG. 3 is a flow diagram of an example method 300 for optimizing waveforms for a neuromodulation device (e.g., implantable medical device 116, shown in FIG. 1). In one embodiment, method 300 is implemented using computer system 104, shown in FIG. 1 (e.g., via a processor of computer system 104) within system 100, shown in FIG. 1. Alternatively, method 300 may be implemented using any suitable computing device. Method 300 may be implemented each time a new neuromodulation therapy is about to begin.

At block 302, computer system 104 retrieves historical waveform data associated with a plurality of waveforms used in therapeutic sessions for a plurality of patients 110. The historical waveform data includes a plurality of waveform parameters. The waveform parameters for a tonic waveform may include a frequency, a pulse-width, and an amplitude, and the waveform parameters for a burst waveform may include a number of pulses, an intra-burst frequency, an inter-burst frequency, a pulse width, and an amplitude.

At block 304, computer system 104 analyzes the historical waveform parameter data to determine preferred waveform parameters. In an exemplary embodiment, computer system 104 may determine, from the historical waveform parameter data, preferred waveform parameters by determining the most common waveform parameters used in neuromodulation therapy for a population of patients 110 associated with the historical waveform parameter data. The population may include all of the historical waveform parameter data for each of patients 110 associated with the historical waveform parameter data. In another exemplary embodiment, computer system 104 may determine the most common waveform parameters of a sub-set of the population. For example, sub-sets of the population may include patients 110 grouped by one or more of age, height and weight, sex, disorder being treated with the neuromodulation therapy, a beginning pain level (e.g., before the start of the neuromodulation therapy), etc. In these embodiments, computer system 104 may determine the preferred waveform parameters only for the sub-set of the population in which a current patient 110 fits. Preferred waveform parameters may also be set by clinician 114.

At block 306, computer system 104 determines that a current patient 110 is starting a new therapeutic session using a patient therapeutic device (e.g., implantable medical device 116, shown in FIG. 1). Computer system 104 may determine that patient 110 is starting the new therapeutic session when, for example, patient 110 powers on a device (e.g., patient device 108, shown in FIG. 1) to control the patient therapeutic device and/or another user (e.g., clinician 114) power on a device (e.g., clinician device 112, shown in FIG. 1) to control the patient therapeutic device.

At block 308, computer system 104 displays each preferred waveform parameter to current patient 110 (e.g., through patient device 108). In the exemplary embodiment, computer system 104 displays each preferred waveform parameter one at a time. In other embodiments, computer system 104 may display all preferred waveform parameters together.

At block 310, computer system 104 prompts current patients 110 and/or clinician(s) 114 to accept or modify the preferred waveform parameters. For example, computer system may display a question like, "Is 4 Hz a suitable frequency?" and current patient 110 and/or clinician 114 may accept 4 Hz as a suitable frequency, prompt computer system 104 to determine a better frequency, and/or input a specific frequency.

At block 312, computer system 104 optimizes the waveform parameters based upon received user input (e.g., from patient 110 and/or clinician 114). For example, computer system 104 may optimize the waveform parameters if current patient 110 and/or clinician 114 inputs a request that computer system 104 determine different waveform parameters than the preferred waveform parameters. Computer system 104 may optimize the waveform parameters by further analyzing the historical waveform parameter data to optimize the waveform parameters for current patient 110. For example, computer system 104 may analyze historical waveform parameter data to determine which waveform parameters provided the best results for patients 110. Computer system 104 may determine which waveform parameters provided the best results by (i) determining which waveform parameters patients 110 kept after many "guess-and-check" trials, (ii) determining patterns of waveform parameters that give good results (e.g., increasing or decreasing one or more waveform parameters periodically), and (iii) comparing patient input data regarding how the patients 110 feel after the neuromodulation therapy session, if available, to the historical waveform parameter data for the neuromodulation therapy session.

Computer system 104 may utilize machine learning and/or artificial intelligence algorithms to analyze the historical waveform parameter data and patient results of the neuromodulation therapy. Accordingly, computer system 104 may learn the best waveform parameters for individual patients 110 and a population of patients 110. For example, computer system 104 may learn which waveform parameters are best for a specific patient 110 based upon analyzing new waveform parameter data and neuromodulation therapy outcomes associated with specific patient 110 along with the historical waveform parameter data. Further, computer system 104 may determine certain patterns of waveform parameters that lead to the best results for a population of patients 110. Accordingly, the preferred waveform parameters and optimized waveform parameters determined by computer system 104 may periodically change as computer system 104 learns about which waveform parameters provide the best results for patients 110 using neuromodulation therapy.

At block 314, computer system 104 transmits the optimized waveform parameters to the patient therapeutic device (e.g., implantable medical device 116) to start the therapeutic session.

Figure 4:
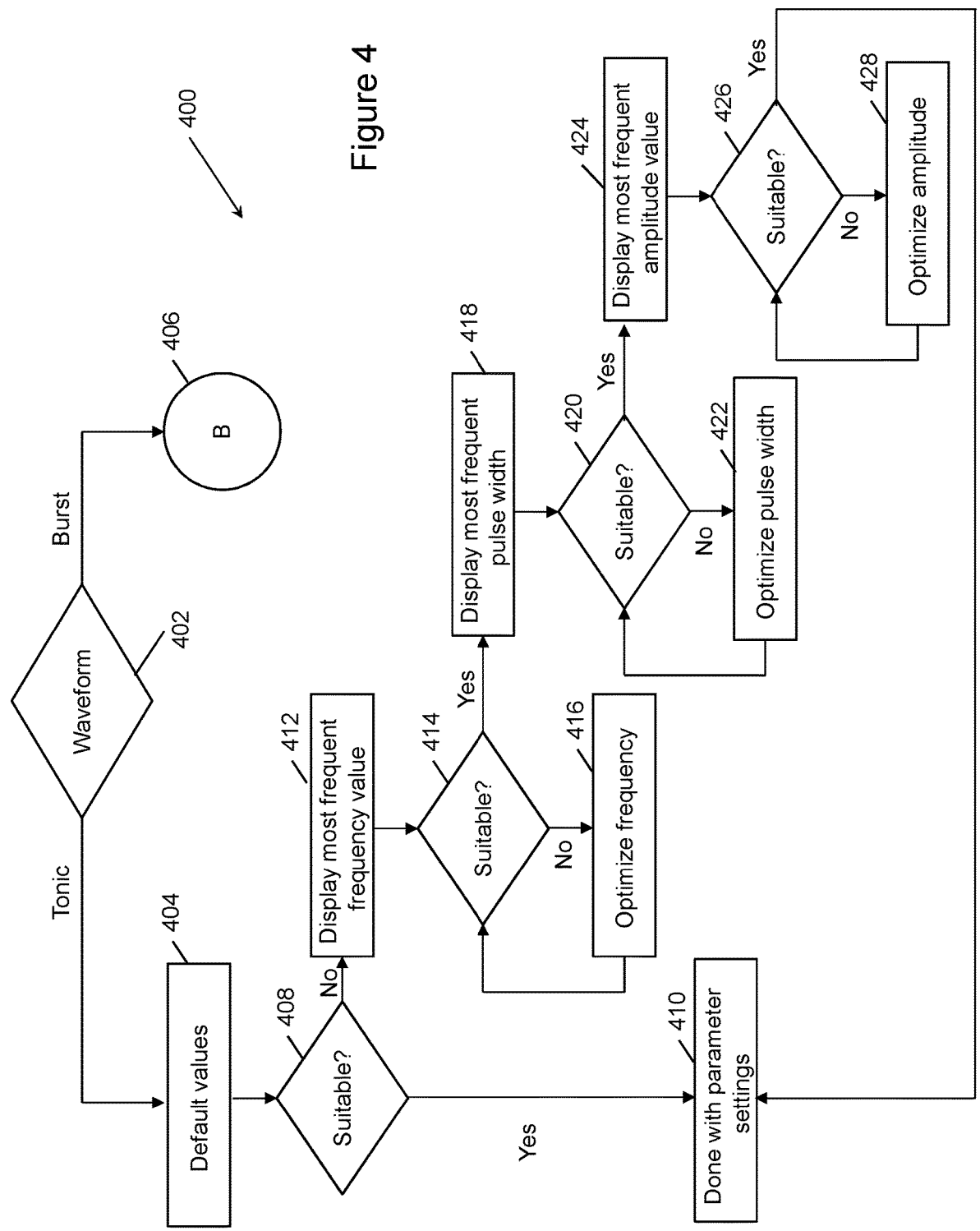
FIG. 4 is a flow diagram of one embodiment of a method for optimizing waveform parameters of an implantable medical device.

FIG. 4 is a flow diagram of an example method 400 for optimizing waveform parameters for waveforms associated with a neuromodulation device (e.g., implantable medical device 116, shown in FIG. 1). In one embodiment, method 400 is implemented by computer system 104, shown in FIG. 1 (e.g., via a processor of computer system 104) within system 100, shown in FIG. 1. Alternatively, method 400 may be implemented using any suitable computing device. Method 400 may be implemented each time a new neuromodulation therapy is about to begin.

At block 402, patient 110 is prompted to input a waveform type. In the illustrated embodiment, patient 110 inputs either a tonic waveform type or a burst waveform type. If patient 110 inputs a tonic waveform type, method 400 continues to block 404. If patient 110 inputs a burst waveform type, method 400 continues to block 406, which is described further with respect to FIG. 5.

At block 404, default values are displayed to patient 110. The default values may be set by a manufacturer of implantable medical device 116 or by clinician 114. The default values are the same for each patient 110.

At block 408, patient 110 is prompted to input whether the default values are suitable for patient 110. If patient 110 inputs that the default values are suitable for patient 110, method 400 continues to block 410. At block 410, the parameters are finalized and the neuromodulation therapy begins. If patient 110 inputs that the default values are not suitable for patient 110, method 400 continues to block 412.

At block 412, the most frequent frequency values are displayed to patient 110. The most frequent frequency values are determined as described above, especially with regard to FIG. 3.

At block 414, patient 110 is prompted to input whether the most frequent frequency values are suitable. If patient 110 inputs that the most frequent frequency values are not suitable, method 400 continues to block 416. If patient 110 inputs that the most frequent frequency values are suitable, method continues to block 418.

At block 416, computer system 104 optimizes the frequency values, as described above, especially with respect to FIG. 3. Once computer system 104 optimizes the frequency values, the optimized frequency values are displayed to patient 110 (e.g., as at block 412). Patient 110 is prompted to input whether the optimized frequency values are suitable. If the optimized frequency values are suitable, method 400 continues to block 418. If the optimized frequency values are not suitable, computer system 104 optimizes the frequency values until the frequency values are suitable to patient 110 such that method 400 may continue to block 418.

At block 418, the most frequent pulse width values are displayed to patient 110. The most frequent pulse width values are determined as described above, especially with regard to FIG. 3.

At block 420, patient 110 is prompted to input whether the most frequent pulse width values are suitable. If patient 110 inputs that the most frequent frequency values are not suitable, method 400 continues to block 422. If patient 110 inputs that the most frequent frequency values are suitable, method continues to block 424.

At block 422, computer system 104 optimizes the pulse width values, as described above, especially with respect to FIG. 3. Once computer system 104 optimizes the pulse width values, the optimized pulse width values are displayed to patient 110 (e.g., as at block 418). Patient 110 is prompted to input whether the optimized pulse width values are suitable. If the optimized pulse width values are suitable, method 400 continues to block 424. If the optimized frequency values are not suitable, computer system 104 optimizes the pulse width values until the pulse width values are suitable to patient 110 such that method 400 may continue to block 424.

At block 424, the most frequent amplitude values are displayed to patient 110. The most frequent amplitude values are determined as described above, especially with regard to FIG. 3.

At block 426, patient 110 is prompted to input whether the most frequent amplitude values are suitable. If patient 110 inputs that the most frequent amplitude values are not suitable, method 400 continues to block 428. If patient 110 inputs that the most frequent frequency values are suitable, method continues to block 410. At block 410, the parameters are finalized and the neuromodulation therapy begins.

At block 428, computer system 104 optimizes the amplitude values, as described above, especially with respect to FIG. 3. Once computer system 104 optimizes the amplitude values, the optimized amplitude values are displayed to patient 110 (e.g., as at block 424). Patient 110 is prompted to input whether the optimized frequency values are suitable. If the optimized frequency values are suitable, method 400 continues to block 410, where the parameters are completed and neuromodulation therapy can begin. If the optimized amplitude values are not suitable, computer system 104 optimizes the amplitude values until the amplitude values are suitable to patient 110 such that method 400 may continue to block 410.

Figure 5:
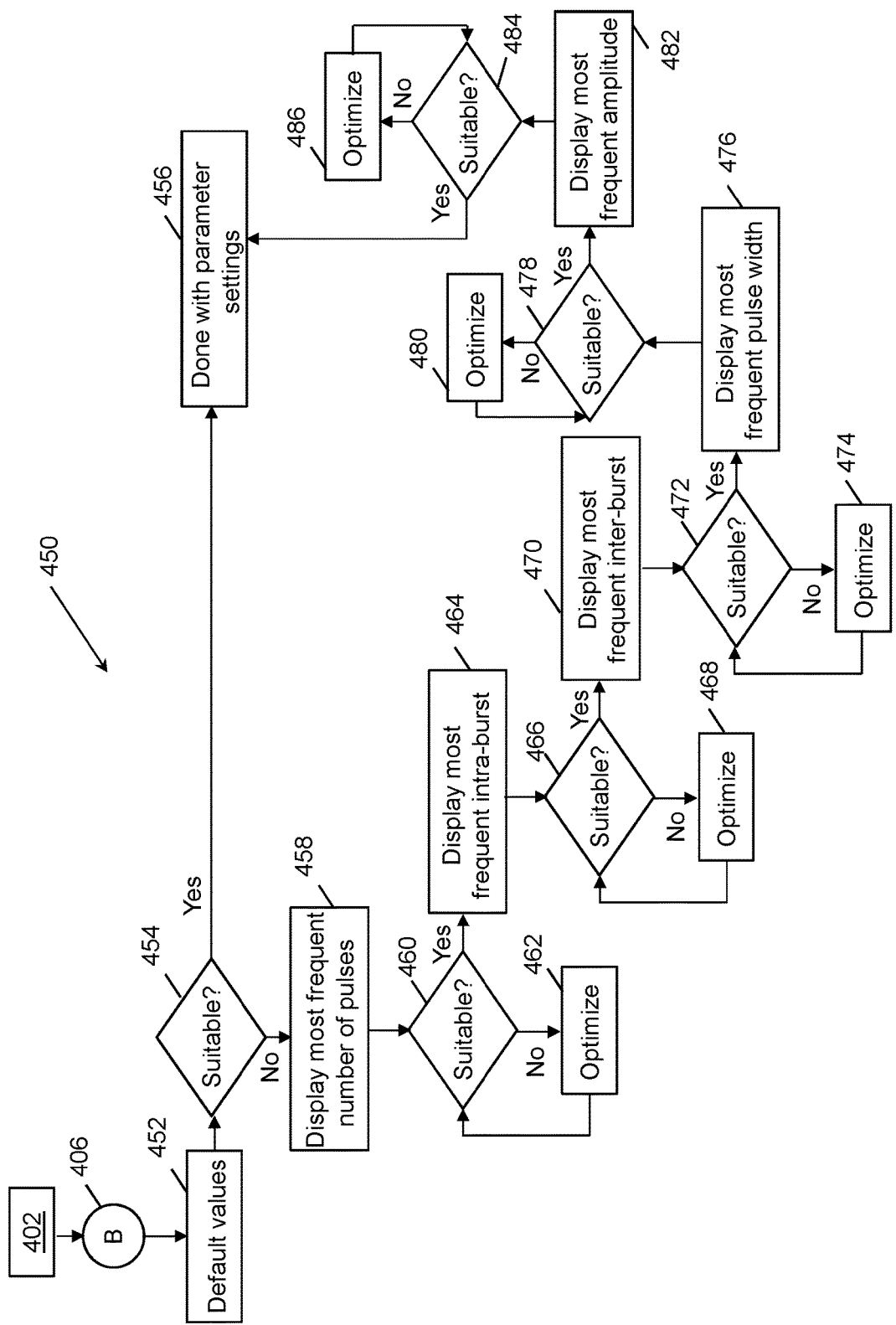
FIG. 5 is a flow diagram of another embodiment of a method for optimizing waveform parameters of an implantable medical device.

FIG. 5 is a flow diagram of an example method 450 for optimizing waveform parameters for burst waveforms associated with a neuromodulation device (e.g., implantable medical device 116, shown in FIG. 1). Method 450 is substantially similar to method 400, shown in FIG. 4, except method 450 includes additional waveform parameters that are optimized. In one embodiment, method 450 is implemented by computer system 104, shown in FIG. 1 (e.g., via a processor of computer system 104) within system 100, shown in FIG. 1. Alternatively, method 400 may be implemented using any suitable computing device. Method 400 may be implemented each time a new neuromodulation therapy is about to begin.

At block 452, default values are displayed to patient 110. The default values may be set by a manufacturer of implantable medical device 116 or by clinician 114. The default values are the same for each patient 110.

At block 454, patient 110 is prompted to input whether the default values are suitable for patient 110. If patient 110 inputs that the default values are suitable for patient 110, method 450 continues to block 456. At block 456, the parameters are finalized and the neuromodulation therapy begins. If patient 110 inputs that the default values are not suitable for patient 110, method 450 continues to block 458.

At block 458, the most frequent number of pulses is displayed to patient 110. The most frequent number of pulses is determined as described above, especially with regard to FIG. 3.

At block 460, patient 110 is prompted to input whether the most frequent number of pulses is suitable. If patient 110 inputs that the most frequent frequency values are not suitable, method 400 continues to block 462. If patient 110 inputs that the most frequent number of pulses are suitable, method continues to block 464.

At block 462, computer system 104 optimizes the number of pulses, as described above, especially with respect to FIG. 3. Once computer system 104 optimizes the number of pulses, the optimized number of pulses is displayed to patient 110 (e.g., as at block 458). Patient 110 is prompted to input whether the optimized number of pulses is suitable. If the optimized number of pulses is suitable, method 400 continues to block 464. If the optimized number of pulses is not suitable, computer system 104 optimizes the number of pulses until the number of pulses is suitable to patient 110 such that method 400 may continue to block 464.

At block 464, the most frequent intra-burst frequency values are displayed to patient 110. The most frequent intra-burst frequency values are determined as described above, especially with regard to FIG. 3.

At block 466, patient 110 is prompted to input whether the most frequent intra-burst frequency values are suitable. If patient 110 inputs that the most frequent intra-burst frequency values are not suitable, method 400 continues to block 468. If patient 110 inputs that the most frequent intra-burst frequency values are suitable, method continues to block 470.

At block 468, computer system 104 optimizes the intra-burst frequency values, as described above, especially with respect to FIG. 3. Once computer system 104 optimizes the intra-burst frequency values, the optimized pulse width values are displayed to patient 110 (e.g., as at block 464). Patient 110 is prompted to input whether the optimized intra-burst frequency values are suitable. If the optimized intra-burst frequency values are suitable, method 400 continues to block 470. If the optimized intra-burst frequency values are not suitable, computer system 104 optimizes the intra-burst frequency values until the intra-burst frequency values are suitable to patient 110 such that method 400 may continue to block 470.

At block 470, the most frequent inter-burst frequency values are displayed to patient 110. The most frequent inter-burst frequency values are determined as described above, especially with regard to FIG. 3.

At block 472, patient 110 is prompted to input whether the most frequent inter-burst frequency values are suitable. If patient 110 inputs that the most frequent inter-burst frequency values are not suitable, method 400 continues to block 474. If patient 110 inputs that the most frequent inter-burst frequency values are suitable, method continues to block 476.

At block 474, computer system 104 optimizes the inter-burst frequency values, as described above, especially with respect to FIG. 3. Once computer system 104 optimizes the inter-burst frequency values, the optimized inter-burst frequency values are displayed to patient 110 (e.g., as at block 470). Patient 110 is prompted to input whether the optimized inter-burst frequency values are suitable. If the optimized inter-burst frequency values are suitable, method 400 continues to block 476. If the optimized inter-burst frequency values are not suitable, computer system 104 optimizes the inter-burst frequency values until the inter-burst frequency values are suitable to patient 110 such that method 400 may continue to block 476.

At block 476, the most frequent pulse width values are displayed to patient 110. The most frequent pulse width values are determined as described above, especially with regard to FIG. 3.

At block 478, patient 110 is prompted to input whether the most frequent pulse width values are suitable. If patient 110 inputs that the most frequent pulse width values are not suitable, method 400 continues to block 480. If patient 110 inputs that the most frequent pulse width values are suitable, method continues to block 482.

At block 480, computer system 104 optimizes the pulse width values, as described above, especially with respect to FIG. 3. Once computer system 104 optimizes the pulse width values, the optimized pulse width values are displayed to patient 110 (e.g., as at block 476). Patient 110 is prompted to input whether the optimized pulse width values are suitable. If the optimized pulse width values are suitable, method 400 continues to block 482. If the optimized pulse width values are not suitable, computer system 104 optimizes the pulse width values until the pulse width values are suitable to patient 110 such that method 400 may continue to block 482.

At block 482, the most frequent amplitude values are displayed to patient 110. The most frequent amplitude values are determined as described above, especially with regard to FIG. 3.

At block 484, patient 110 is prompted to input whether the most frequent amplitude values are suitable. If patient 110 inputs that the most frequent amplitude values are not suitable, method 400 continues to block 486. If patient 110 inputs that the most frequent pulse width values are suitable, method continues to block 456. At block 456, the parameters are finalized and the neuromodulation therapy begins.

At block 486, computer system 104 optimizes the amplitude values, as described above, especially with respect to FIG. 3. Once computer system 104 optimizes the amplitude values, the optimized amplitude values are displayed to patient 110 (e.g., as at block 482). Patient 110 is prompted to input whether the optimized amplitude values are suitable. If the optimized amplitude values are suitable, method 400 continues to block 456, where the parameters are completed and neuromodulation therapy can begin. If the optimized amplitude values are not suitable, computer system 104 optimizes the amplitude values until the amplitude values are suitable to patient 110 such that method 400 may continue to block 456.

Although FIGS. 4 and 5 show methods 400 and 450 in a specific order of optimization, it should be understood that, in other embodiments, the methods 400 and 450 do not have to be arranged in the specific order illustrated in FIGS. 4 and 5. For example, in other embodiments, method 400 may optimize frequency at block 416, optimize amplitude at block 428, and then optimize pulse width at block 422.

Further, in some embodiments, methods 400 and 450 may be iterative (e.g., methods 400 and 450 may be performed repeatedly). In other embodiments, methods 400 and 450 may follow a specific sampling scheme. For example, methods 400 and 450 may follow Gibbs sampling.

Figure 6:
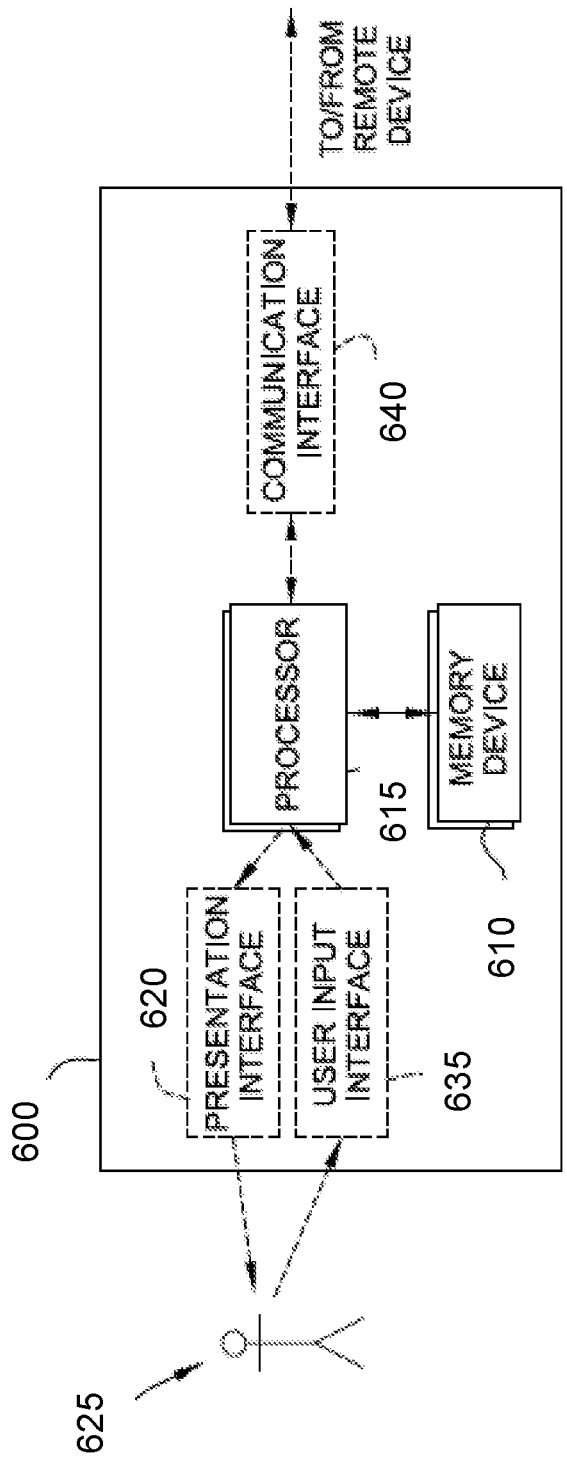
FIG. 6 is a block diagram of one embodiment of a computing device.

FIG. 6 illustrates one embodiment of a computing device 600 that may be used to implement the systems and methods described herein. For example, computing device 600 may be used to implement computer system 104, patient device 108 and/or clinician device 112 (all shown in FIG. 1).

Computing device 600 includes at least one memory device 610 and a processor 615 that is coupled to memory device 610 for executing instructions. In some embodiments, executable instructions are stored in memory device 610. In this embodiment, computing device 600 performs one or more operations described herein by programming processor 615. For example, processor 615 may be programmed by encoding an operation as one or more executable instructions and by providing the executable instructions in memory device 610.

Processor 615 may include one or more processing units (e.g., in a multi-core configuration). Further, processor 615 may be implemented using one or more heterogeneous processor systems in which a main processor is present with secondary processors on a single chip. In another illustrative example, processor 615 may be a symmetric multi-processor system containing multiple processors of the same type. Further, processor 615 may be implemented using any suitable programmable circuit including one or more systems and microcontrollers, microprocessors, reduced instruction set circuits (RISC), application specific integrated circuits (ASIC), programmable logic circuits, field programmable gate arrays (FPGA), and any other circuit capable of executing the functions described herein. In one embodiment, processor 615 is a GPU (as opposed to a central processing unit (CPU)). Alternatively, processor 615 may be any processing device capable of implementing the systems and methods described herein.

In this embodiment, memory device 610 is one or more devices that enable information such as executable instructions and/or other data to be stored and retrieved. Memory device 610 may include one or more computer readable media, such as, without limitation, dynamic random access memory (DRAM), static random access memory (SRAM), a solid state disk, and/or a hard disk. Memory device 610 may be configured to store, without limitation, application source code, application object code, source code portions of interest, object code portions of interest, configuration data, execution events and/or any other type of data. In one embodiment, memory device 610 is a GPU memory unit.

Alternatively, memory device 610 may be any storage device capable of implementing the systems and methods described herein.

In this embodiment, computing device 600 includes a presentation interface 620 that is coupled to processor 615. Presentation interface 620 presents information to a user 625 (e.g., patient 110 or clinician 114). For example, presentation interface 620 may include a display adapter (not shown) that may be coupled to a display device, such as a cathode ray tube (CRT), a liquid crystal display (LCD), an organic LED (OLED) display, and/or an "electronic ink" display. In some embodiments, presentation interface 620 includes one or more display devices.

In this embodiment, computing device 600 includes a user input interface 635. User input interface 635 is coupled to processor 615 and receives input from user 625. User input interface 635 may include, for example, a keyboard, a pointing device, a mouse, a stylus, a touch sensitive panel (e.g., a touch pad or a touch screen), a gyroscope, an accelerometer, a position detector, and/or an audio user input interface. A single component, such as a touch screen, may function as both a display device of presentation interface 620 and user input interface 635.

Computing device 600, in this embodiment, includes a communication interface 640 coupled to processor 615. Communication interface 640 communicates with one or more remote devices. To communicate with remote devices, communication interface 640 may include, for example, a wired network adapter, a wireless network adapter, and/or a mobile telecommunications adapter.

The embodiments described herein provide systems and methods for optimizing waveform parameters for neuromodulation therapy. A method includes retrieving historical waveform data associated with a plurality of waveforms used in therapeutic sessions for a plurality of patients, the historical waveform data including a plurality of waveform parameters; analyzing the historical waveform data to determine preferred waveform parameters; determining that a patient is starting a new therapeutic session using the patient therapeutic device; displaying, on a user interface, each of the preferred waveform parameters; prompting the user to accept or modify the displayed waveform parameters; optimizing, based upon the user input, the waveform parameters for the therapeutic session; and transmitting the optimized waveform parameters to the patient therapeutic device to start the therapeutic session.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A computing system for optimizing a waveform, the computing system in communication with an implantable pulse generator, the computing system comprising:
   a computing device including a memory device and a processor communicatively coupled to the memory device, the processor configured to:
   retrieve, from the memory device, historical waveform data associated with a plurality of waveforms used in therapeutic sessions for a population of patients, the historical waveform data including a plurality of waveform parameters, the population of patients including a plurality of patients;
   group each of the plurality of patients into an associated sub-set of a plurality of sub-sets of the population of patients, wherein each sub-set of the plurality of sub-sets groups patients based on at least one of age, height and weight, sex, disorder being treated, and beginning pain level;
   analyze the historical waveform data to determine preferred waveform parameters;
   determine that a patient is starting a new therapeutic session using a patient therapeutic device;
   receive, from the patient therapeutic device, patient data associated with the patient;
   compare the patient data with each of the plurality of sub-sets to determine a particular sub-set of the plurality of sub-sets that corresponds to the patient data;
   determine, from the historical waveform data for the patients grouped in the determined particular sub-set, the preferred waveform parameters for the determined particular sub-set;
   display, on a user interface, each of the preferred waveform parameters for the determined particular sub-set of the population of the patient;
   prompt a user for user input associated with the preferred waveform parameters, the user input including accepting or modifying the preferred waveform parameters;
   optimize, based upon the user input, waveform parameters for the new therapeutic session by analyzing, using at least one of machine learning and artificial intelligence, the historical waveform data for the patients grouped in the determined particular sub-set to determine patterns of the waveform parameters in the historical waveform data that led to desirable results for those patients; and
   transmit the optimized waveform parameters to the patient therapeutic device to start the therapeutic session.

2. The computing system of claim 1, wherein determining each of the preferred waveform parameters causes the processor to be configured to:
 determine, from the historical waveform data, a most frequent value of each of the waveform parameters for the plurality of patients.

3. The computing system of claim 2, wherein the patient data includes at least one of an age, a sex, a height, a weight, an ethnicity, and a current pain level, and wherein the processor is further configured to:
 determine the preferred waveform parameters and the optimized waveform parameters that provide results for the plurality of patients.

4. The computing system of claim 1, wherein the processor is further configured to:
 prompt the user to input a type of waveform to be used in the new therapeutic session, wherein the type of waveform is a tonic waveform or a burst waveform.

5. The computing system of claim 4, wherein the processor is further configured to determine the preferred waveform parameters based upon the type of waveform.

6. The computing system of claim 5, wherein the waveform parameters for (i) the tonic waveform include a frequency, a pulse-width, and an amplitude or for (ii) the burst waveform include a number of pulses, an intra-burst frequency, an inter-burst frequency, a pulse width, and an amplitude.

7. A method for optimizing a waveform, the method implemented by a computing system in communication with an implantable pulse generator, the computing system including a processor in communication with a memory device, the method comprising:
 retrieving, from the memory device, historical waveform data associated with a plurality of waveforms used in therapeutic sessions for a population of patients, the historical waveform data including a plurality of waveform parameters, the population of patients including a plurality of patients;
 grouping each of the plurality of patients into an associated sub-set of a plurality of sub-sets of the population of patients, wherein each sub-set of the plurality of sub-sets groups patients based on at least one of age, height and weight, sex, disorder being treated, and beginning pain level;
 analyzing the historical waveform data to determine preferred waveform parameters;
 determining that a patient is starting a new therapeutic session using a patient therapeutic device;
 receiving, from the patient therapeutic device, patient data associated with the patient;
 comparing the patient data with each of the plurality of sub-sets to determine a particular sub-set of the plurality of sub-sets that corresponds to the patient data;
 determining, from the historical waveform data for the patients grouped in the determined particular sub-set, the preferred waveform parameters for the determined particular sub-set;
 displaying, on a user interface, each of the preferred waveform parameters for the determined particular sub-set of the population of the patient;
 prompting a user for user input associated with the preferred waveform parameters, the user input including accepting or modifying the preferred waveform parameters;
 optimizing, based upon the user input, waveform parameters for the new therapeutic session by analyzing, using at least one of machine learning and artificial intelligence, the historical waveform data for the patients grouped in the determined particular sub-set to determine patterns of the waveform parameters in the historical waveform data that led to desirable results for those patients; and
 transmitting the optimized waveform parameters to the patient therapeutic device to start the therapeutic session.

8. The method of claim 7, wherein determining each of the preferred waveform parameters comprises:
 determining, from the historical waveform data, a most frequent value of each of the waveform parameters for the plurality of patients.

9. The method of claim 8, wherein the patient data includes at least one of an age, a sex, a height, a weight, an ethnicity, and a current pain level, and wherein the method further comprises:
 determining the preferred waveform parameters and the optimized waveform parameters that provide results for the plurality of patients.

10. The method of claim 7 further comprising:
 prompting the user to input a type of waveform to be used in the new therapeutic session, wherein the type of waveform is a tonic waveform or a burst waveform.

11. The method of claim 10 further comprising determining the preferred waveform parameters based upon the type of waveform.

12. The method of claim 11, wherein the waveform parameters for (i) the tonic waveform include a frequency, a pulse-width, and an amplitude or for (ii) the burst waveform include a number of pulses, an intra-burst frequency, an inter-burst frequency, a pulse width, and an amplitude.

13. Non-transitory computer-readable media having computer-executable instructions thereon, wherein when executed by a processor of a computing device communicatively coupled to a memory device, cause the processor of the computing device to:
 retrieve, from the memory device, historical waveform data associated with a plurality of waveforms used in therapeutic sessions for a population of patients, the historical waveform data including a plurality of waveform parameters, the population of patients including a plurality of patients;
 group each of the plurality of patients into an associated sub-set of a plurality of sub-sets of the population of patients, wherein each sub-set of the plurality of sub-sets groups patients based on at least one of age, height and weight, sex, disorder being treated, and beginning pain level;
 analyze the historical waveform data to determine preferred waveform parameters;
 determine that a patient is starting a new therapeutic session using a patient therapeutic device;
 receive, from the patient therapeutic device, patient data associated with the patient;
 compare the patient data with each of the plurality of sub-sets to determine a particular sub-set of the plurality of sub-sets that corresponds to the patient data;
 determine, from the historical waveform data for the patients grouped in the determined particular sub-set, the preferred waveform parameters for the determined particular sub-set;
 display, on a user interface, each of the preferred waveform parameters for the determined particular sub-set of the population of the patient;

prompt a user for user input associated with the preferred waveform parameters, the user input including accepting or modifying the preferred waveform parameters;

optimize, based upon the user input, waveform parameters for the new therapeutic session by analyzing, using at least one of machine learning and artificial intelligence, the historical waveform data for the patients grouped in the determined particular sub-set to determine patterns of the waveform parameters in the historical waveform data that led to desirable results for those patients; and transmit optimized waveform parameters to the patient therapeutic device to start the therapeutic session.

14. The non-transitory computer-readable media of claim 13, wherein the computer-executable instructions further cause the processor to:

determine, from the historical waveform data, a most frequent value of each of the waveform parameters for the plurality of patients.

15. The non-transitory computer-readable media of claim 14, wherein the patient data includes at least one of an age, a sex, a height, a weight, an ethnicity, and a current pain level, and wherein the computer-executable instructions further cause the processor to:

determine the preferred waveform parameters and the optimized waveform parameters that provide results for the plurality of patients.

16. The non-transitory computer-readable media of claim 13, wherein the computer-executable instructions further cause the processor to:

prompt the user to input a type of waveform to be used in the new therapeutic session, wherein the type of waveform is a tonic waveform or a burst waveform.

17. The non-transitory computer-readable media of claim 16, wherein the computer-executable instructions further cause the processor to determine the preferred waveform parameters based upon the type of waveform.

18. The computing system of claim 1, wherein to determine patterns of the waveform parameters in the historical waveform data that led to desirable results, the processor is configured to determine the patterns based on at least one of i) particular waveform parameters that were maintained after multiple trials and ii) patient input data providing feedback on the waveform parameters in the historical waveform data.

* * * * *